United States Patent
Matsushita et al.

(10) Patent No.: US 9,402,115 B2
(45) Date of Patent: Jul. 26, 2016

(54) MONITORING SYSTEM, NOTIFICATION APPARATUS AND MONITORING METHOD

(71) Applicant: TOSHIBA TEC KABUSHIKI KAISHA, Shinagawa-ku, Tokyo (JP)

(72) Inventors: Naohiro Matsushita, Shizuoka (JP); Shinji Saegusa, Shizuoka (JP); Hiroshi Hashidume, Tokyo-to (JP)

(73) Assignee: TOSHIBA TEC KABUSHIKI KAISHA, Tokyo (JP)

( * ) Notice: Subject to any disclaimer, the term of this patent is extended or adjusted under 35 U.S.C. 154(b) by 93 days.

(21) Appl. No.: 14/215,244

(22) Filed: Mar. 17, 2014

(65) Prior Publication Data
US 2015/0061838 A1    Mar. 5, 2015

(30) Foreign Application Priority Data
Sep. 4, 2013   (JP) .................................. 2013-183043

(51) Int. Cl.
| H04Q 5/22 | (2006.01) |
| H04Q 9/00 | (2006.01) |
| F16B 31/02 | (2006.01) |
| B25B 23/142 | (2006.01) |
| G01L 5/24 | (2006.01) |

(52) U.S. Cl.
CPC *H04Q 9/00* (2013.01); *F16B 31/02* (2013.01); *B25B 23/1425* (2013.01); *G01L 5/24* (2013.01); *G01N 2291/2691* (2013.01)

(58) Field of Classification Search
CPC ........ F16B 31/02; G01L 5/24; B25B 23/1425
See application file for complete search history.

(56) References Cited

U.S. PATENT DOCUMENTS

| 7,246,980 B2 * | 7/2007 | Azzalin .......................... 292/327 |
| 7,412,898 B1 * | 8/2008 | Smith ........................ G01L 5/24 73/761 |

(Continued)

FOREIGN PATENT DOCUMENTS

| JP | 2001-023075 | 1/2001 |
| JP | 2005-182289 | 7/2005 |

(Continued)

OTHER PUBLICATIONS

Japanese Office Action for Japanese Application No. 2013-183043 mailed on Jul. 7, 2015.

(Continued)

*Primary Examiner* — Omeed Alizada
(74) *Attorney, Agent, or Firm* — Amin, Turocy & Watson LLP; Gregory Turocy

(57) ABSTRACT

Generally, in accordance with one embodiment, a monitoring system comprises a sensor, a wireless tag, a reader and a notification apparatus. The sensor is correspondingly arranged in a structure. The wireless tag is a passive wireless tag which is correspondingly arranged in the structure to send identification information and measurement information of the sensor by using received electromagnetic wave as a drive source. The reader communicates with the wireless tag to acquire the identification information and the measurement information. The notification apparatus acquires the identification information and the measurement information from the reader, detects a wireless tag or a structure serving as a notification target based on the identification information and the measurement information, and notifies the notification target.

3 Claims, 3 Drawing Sheets

(56) References Cited

U.S. PATENT DOCUMENTS

| | | | |
|---|---|---|---|
| 7,441,462 B2 * | 10/2008 | Kibblewhite | F16B 31/02 73/761 |
| 2009/0058634 A1 * | 3/2009 | Maltseff | H04Q 9/00 340/539.11 |
| 2010/0316316 A1 * | 12/2010 | Kamel | G01D 5/3473 384/448 |

FOREIGN PATENT DOCUMENTS

| | | |
|---|---|---|
| JP | 2005-275554 | 9/2005 |
| JP | 2007-310506 | 11/2007 |
| JP | 2008-90599 | 3/2008 |
| JP | 2012-150895 | 8/2012 |
| JP | 2012-212284 | 11/2012 |

OTHER PUBLICATIONS

Office Action of Notification of Reason(s) for Refusal for Japanese Patent Application No. 2013-183043 dated Mar. 3, 2016, 3 pages.
Decision of Refusal and Decision to Dismiss the Amendment for Japanese Patent Application No. 2013-183043 dated May 17, 2016, 7 pages.

* cited by examiner

MONITORING SYSTEM, NOTIFICATION APPARATUS AND MONITORING METHOD

CROSS-REFERENCE TO RELATED APPLICATION

This application is based upon and claims the benefit of priority from Japanese Patent Application No. 2013-183043, filed Sep. 4, 2013, the entire contents of which are incorporated herein by reference.

FIELD

Embodiments described herein relate to a monitoring technology.

BACKGROUND

Conventionally, a social infrastructure (e.g. road and bridge, tunnel and underpass) is inspected periodically so that an aged position can be found and maintained through component replacement and reinforcement work. To conducting the periodic inspection, the operator goes to the social infrastructure to try to find an abnormal position through a visual inspection and a detailed technical inspection.

However, with the social development, more and more social infrastructures are built, and the number of infrastructures needing inspection is increased. In addition, after a social infrastructure is built, more and more positions are aged with the time elapsing, as a result, the positions in one social infrastructure needing inspection are increased. Thus, the supply of the periodic inspection carried out by operators cannot catch up with needs of the periodic inspection.

There is known a monitoring system which uses a camera arranged in a terminal facility of an emergency telephone at a roadside (for example, see Japanese Unexamined Patent Application Publication No. 2001-23075). In this system, each camera is used to capture the condition of each road and the captured image is sent to a center facility through a telephone line so that the condition of each road can be monitored by the center facility.

DETAILED DESCRIPTION

Generally, in accordance with one embodiment, a monitoring system comprises a sensor, a wireless tag, a reader and a notification apparatus. The sensor is correspondingly arranged in a structure. The wireless tag is a passive wireless tag which is correspondingly arranged in the structure to send identification information and measurement information of the sensor by using received electromagnetic wave as a drive source. The reader communicates with the wireless tag to acquire the identification information and the measurement information. The notification apparatus acquires the identification information and the measurement information from the reader, detects a wireless tag or a structure serving as a notification target based on the identification information and the measurement information, and notifies the notification target.

Generally, in accordance with one embodiment, the notification apparatus comprises a communication section, a detection section and a notification section. The communication section communicates with the reader which acquired the identification information of the wireless tag and the measurement information of the sensor from the passive wireless tag which is correspondingly arranged in the structure and is capable of communicating with the sensor correspondingly arranged in the structure, thereby acquiring the identification information and the measurement information. The detection section detects a wireless tag or a structure serving as a notification target based on the identification information and the measurement information. The notification section notifies the notification target.

Typically, in accordance with one embodiment, a monitoring method including: acquiring, using a reader, the identification information of a passive wireless tag and the measurement information of a sensor from the passive wireless tag which is correspondingly arranged in a structure and is capable of communicating with the sensor correspondingly arranged in the structure; detecting a wireless tag or a structure serving as a notification target based on the identification information and the measurement information; and notifying the notification target.

Embodiments of the present invention are described below with reference to accompanying drawings.

Figure 1:
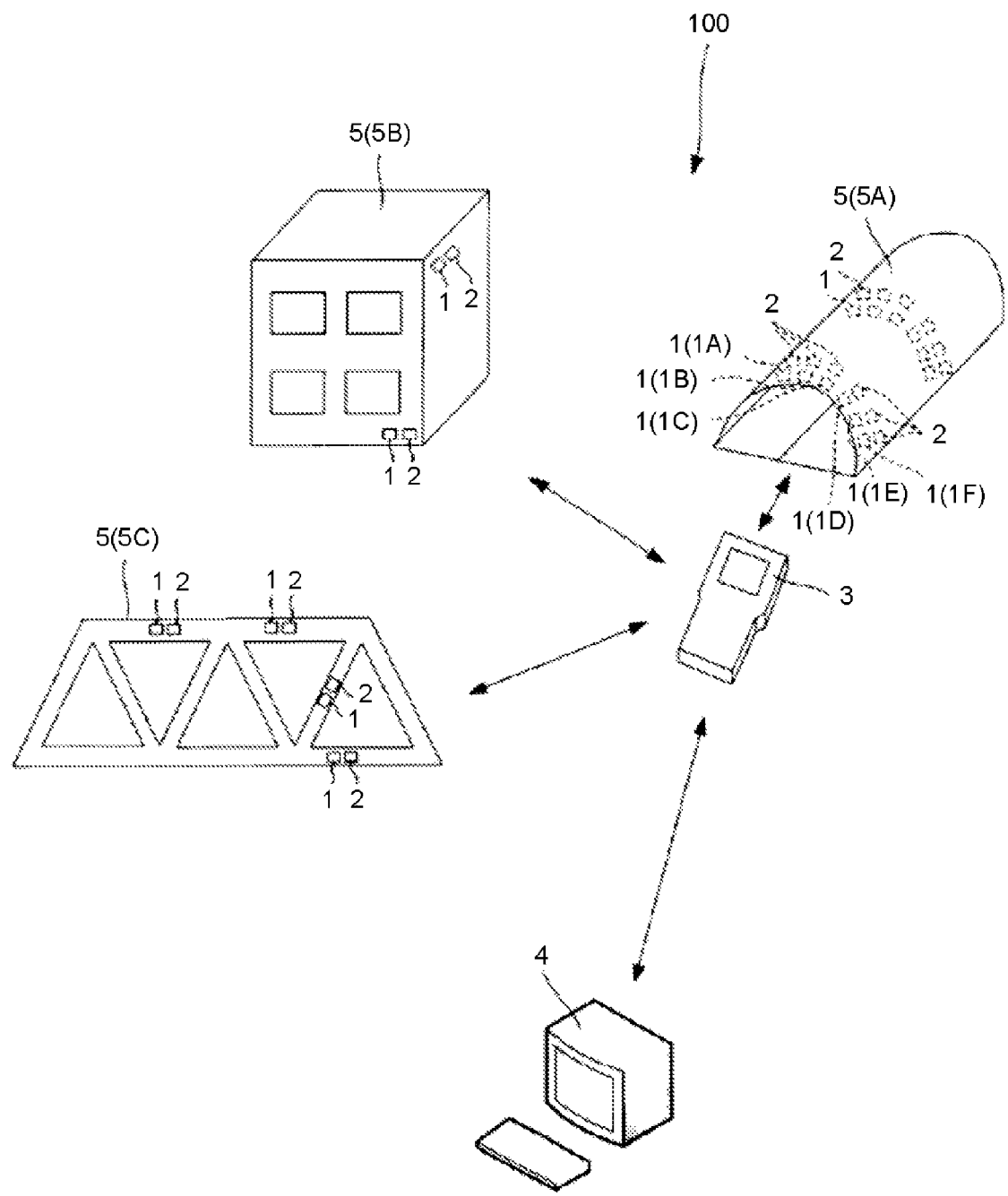
FIG. 1 is a diagram schematically illustrating a social infrastructure monitoring system.

FIG. 1 is a diagram schematically illustrating a monitoring system 100 of a social infrastructure (structure) 5.

The monitoring system 100 comprises a sensor 1, a wireless tag 2, a reader 3 and a PC (Personal Computer) 4.

The sensor 1 is correspondingly arranged at a position of a social infrastructure 5 where inspection is needed. The social infrastructure 5 (hereinafter recorded as an infrastructure 5) may be a tunnel 5A in an urban area or a mountainous area, a building 5B or a bridge 5C. In the present embodiment, it is described that a plurality of sensors 1 are arranged in each infrastructure 5, however, it can also be set that only one sensor 1 is arranged in each infrastructure 5.

The sensor 1 is, for example, an illuminance sensor 1A which is mounted on an illumination device in the tunnel 5A to detect the illuminance of the illumination. The illuminance sensor 1A is used to monitor whether or not illuminance is reduced due to the damage of the illumination device or the use of a bulb. The sensor 1 may also be a humidity sensor 1B for detecting the humidity in the tunnel 5A or a temperature sensor 1C for detecting the temperature in the tunnel 5A. Further, the sensor 1 may also be an impact sensor 1D for detecting the impact applied to the internal wall surface of the tunnel 5A, an inclination sensor 1E for detecting the inclination of the internal wall surface of the tunnel 5A, or a stress sensor for detecting the stress applied to the internal wall surface of the tunnel 5A.

The sensor 1 may also be arranged in a building 5B and a bridge 5C to acquire measurement information such as impact, inclination, illuminance, humidity, temperature and the like.

Moreover, the sensor 1 uses a battery 13 (refer to FIG. 2) as a drive source which, however, may also be a solar cell panel, a wind power generator or a vibration generator that obtains energy from the outside to generate power. The sensor 1 may be integrated with the under-mentioned passive wireless tag 2 to use the power generated by the wireless tag 2 from the electromagnetic wave received from the reader 3 as a drive source.

The wireless tag 2, along with the sensor 1, is correspondingly arranged at a position of the social infrastructure 5 (e.g. tunnel 5A, building 5B or bridge 5C) where inspection is needed. The wireless tag 2 is a passive RFID (Radio Frequency Identification) using the electromagnetic wave received from the reader 3 as a drive source.

The wireless tag 2 is a UHF (Ultra High Frequency) band the communication frequency of which is, for example, 900 MHz and the communication distance of which is 1-5 m. When receiving electromagnetic wave containing an interrogation signal from the reader 3, the wireless tag 2 uses the electromagnetic wave as a drive source to output, to the reader 3, electromagnetic wave containing identification information and the measurement information detected by the sensor 1 serving as a response signal.

The reader 3 is a portable device capable of communicating with the wireless tag 2. When receiving the electromagnetic wave containing the identification information and the measurement information from the wireless tag 2, the reader 3 stores the measurement information in association with the identification information.

The operator tours among wireless tags 2 of different infrastructures 5 to acquire identification information and measurement information from each wireless tag 2 using the reader 3. Then, the operator sends the identification information of each wireless tag 2 and the measurement information associated with the identification information of each wireless tag 2 from the reader 3 to the PC 4.

When receiving the identification information of each wireless tag 2 and the measurement information associated with the identification information of each wireless tag 2 from the reader 3, the PC 4 analyzes the identification information and the measurement information. Then, the PC 4 detects an abnormal wireless tag 2 or social infrastructure 5 serving as a notification target and notifies the notification target to the operator.

In this way, in the monitoring system 100 of the present embodiment, as measurement information is acquired from the wireless tag 2 arranged in the infrastructure 5 using the reader 3, the infrastructure 5 in wooded mountains can be monitored.

In the present embodiment, due to the use of the battery-free passive wireless tag 2, the cost of the wireless tag 2 is reduced when compared with that of an active wireless tag 2 needing a battery.

In the monitoring system 100 described herein, the wireless tag 2 integrated with the sensor 1 may be used; as a result, the wireless tag 2 can be arranged directly, saving the expense on the inspection and replacement of a battery.

In the present embodiment, owing to the use of the passive wireless tag 2, the intensity of the electromagnetic wave output from the wireless tag 2 is reduced compared with that of the electromagnetic wave output from an active wireless tag, therefore, it is almost impossible that the reader 3 is enabled to operate by other electromagnetic waves by mistake, and additionally, the wireless tags 2 can be arranged at a high density. Thus, the monitoring system 100 described herein can be applied in a case where the wireless tags 2 is arranged in an infrastructure 5 in an urban area, or in a case where the wireless tags 2 are arranged at a high density.

Further, in the present embodiment, it is described that the operator goes to the position of the wireless tag 2 of each infrastructure 5 and reads the wireless tag 2 using the reader 3, however, the reader 3 may also be arranged, for example, at the lower part of a train to automatically read the wireless tag arranged on the rail or the guard wall as the train runs. Further, it can also be set that the reader 3 is arranged in a car to automatically read the wireless tags arranged in the tunnel 5A as the car runs in the tunnel 5A.

Hereinafter, each component in the constitutions 1-4 and the infrastructure monitoring method based on the monitoring system 100 are briefly described.

Figure 2:
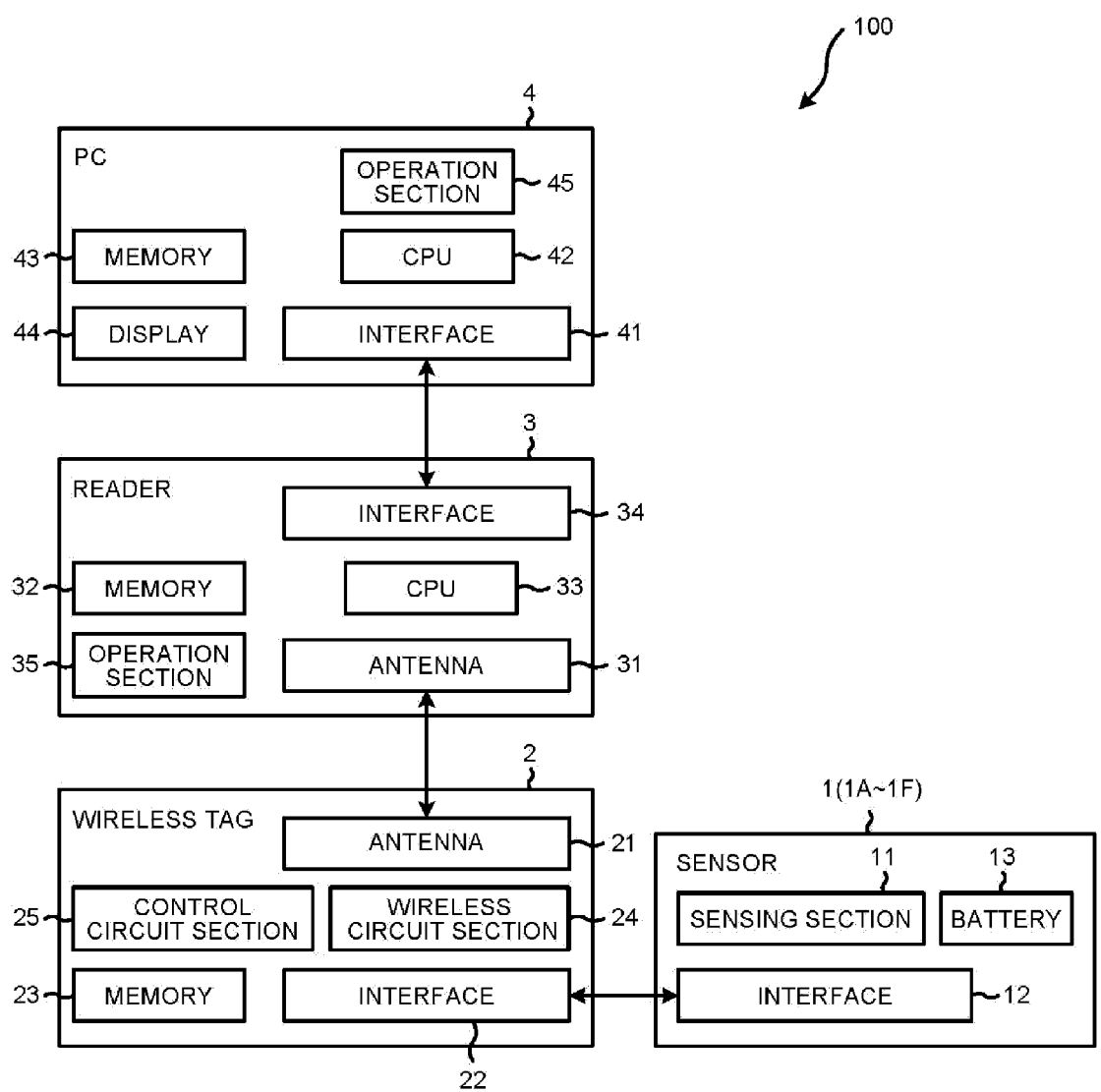
FIG. 2 is a block diagram illustrating a monitoring system.

FIG. 2 is a block diagram illustrating the monitoring system 100.

The sensor 1 (1A-1F) is arranged in the infrastructure 5 such as a tunnel 5A, a building 5B or a bridge 5C. The sensor 1 is connected with the wireless tag 2 through wiring. The sensor acquires measurement information such as illuminance, humidity, temperature, impact and inclination using a sensing section 11 and outputs the measurement information to the wireless tag 2 via an interface 12. The battery 13 supplies power for the sensing section 11 and the interface 12.

The wireless tag 2 is a passive wireless tag which uses received electromagnetic wave as a drive source and is arranged, along with the sensor 1, at a position of the social infrastructure 5 (e.g. tunnel 5A, building 5B or bridge 5C) where inspection is needed. A wireless circuit section 24 of the wireless tag 2 acquires power from the electromagnetic wave received by an antenna 21, and then rectifies and boosts the power. If the electromagnetic wave containing an interrogation signal is received via the antenna 21, a control circuit section 25 of the wireless tag 2 is enabled to operate by the power generated by the wireless circuit section 24 to acquire measurement information from the sensor 1 via an interface 22. Then, the control circuit section 25 controls the wireless circuit section 24 to output, through the antenna 21, the identification information and the measurement information stored in a memory 23 to the reader 3 as a response signal.

A CPU 33 (Central Processing Unit) of the reader 3 sends the interrogation signal to the wireless tag 2 via an antenna 31 according to an instruction received by an operation section 35 from the operator. If the identification information and the measurement information are received from the wireless tag 2 as a response signal, the CPU 33 stores the measurement information in the memory 32 in association with the identification information of each wireless tag 2. If there is a request from the PC 4, the CPU 33 sends the associated identification information and measurement information to the PC 4 via an interface 34.

A CPU 42 (detection section) of the PC 4 (notification apparatus) acquires the identification information of each wireless tag 2 and the measurement information from each wireless tag 2 from the reader 3 via an interface 41 (communication section) according to an instruction of the operator received by an operation section 45, analyzes the acquired identification information and measurement information, and detects a wireless tag 2 or an infrastructure 5 serving as a notification target.

Specifically, the arrangement location of each sensor 1 and a threshold value corresponding to the category of each sensor 1 are stored in a memory 43. Further, the identification information of each wireless tag 2 is associated with the infrastructure 5 provided with the wireless tag 2 in advance and then stored in the memory 43.

The CPU 42 compares the acquired measurement information with the arrangement location of each sensor 1 and the threshold value stored in the memory 43 corresponding to the category of each sensor 1. If the measurement information such as the illuminance in a tunnel 5A is below the threshold value, the CPU 42 determines that abnormality such as the function loss of the illumination device in the tunnel 5A occurs, and displays the wireless tag 2 the identification information of which is associated with the measurement information and the infrastructure 5 provided with the wireless tag 2 on a display (notification section) to notify the target having an abnormality to the operator.

Figure 3:
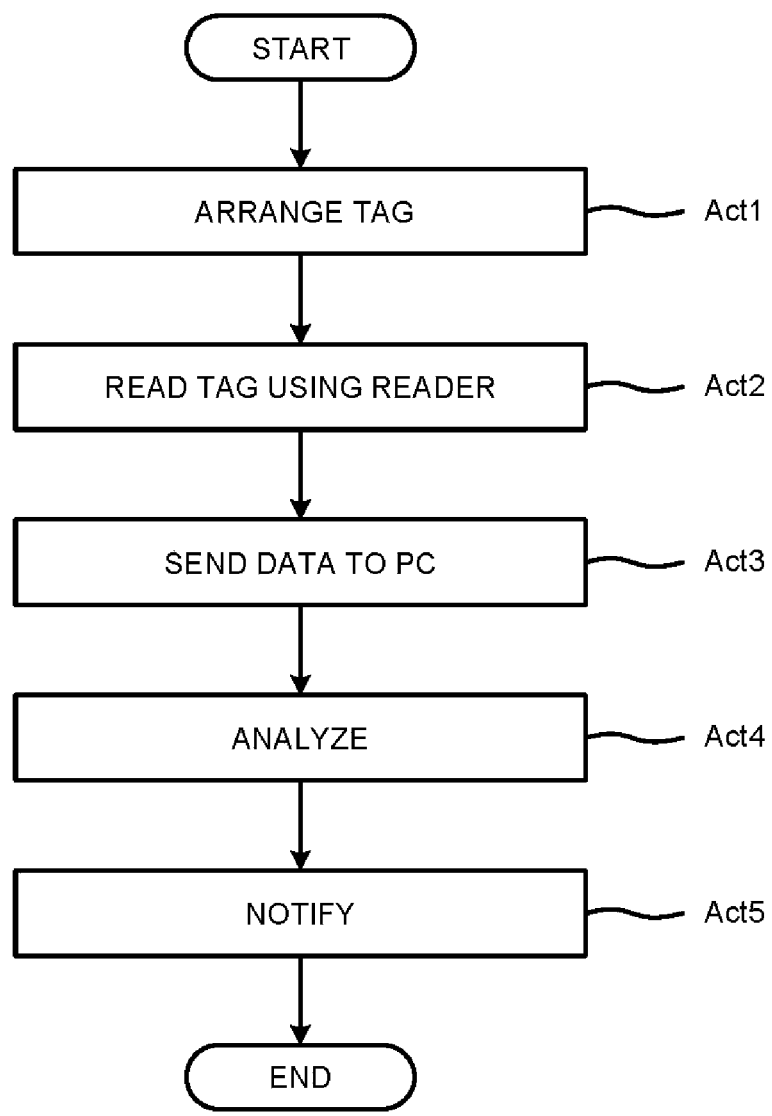
FIG. 3 is a flowchart illustrating an infrastructure monitoring method.

FIG. 3 is a flowchart illustrating an infrastructure monitoring method based on the monitoring system 100.

The operator arranges the sensor 1 and the passive wireless tag 2 at proper positions of the infrastructure 5 such as a tunnel 5A, a building 5B and a bridge 5C according to the category of the sensor 1 (ACT 1).

The operator periodically goes to the position of each wireless tag 2 of the infrastructure 5 to acquire identification information and measurement information from each wireless tag 2 using the reader 3. The reader 3 stores the identification information of each wireless tag 2 in the memory 23 in association with the measurement information (ACT 2).

The PC 4 is manually connected with the reader 3 by the operator through a USB (Universal Serial Bus) connection to acquire the identification information of each wireless tag 2 and the measurement information from each wireless tag 2 (each sensor 1) from the reader 3 (ACT 3).

The PC 4 analyzes the acquired measurement information and compares the acquired measurement information with the arrangement location of each sensor 1 and the threshold value corresponding to the category of each sensor 1 (ACT 4). If the measurement information is below the threshold value, for example, if the illuminance information of an illumination device in a tunnel 5A is below the threshold value, the CPU 42 determines that the function of the illumination device is lost.

The CPU 42 displays the wireless tag 2 the identification information of which is associated with the abnormal measurement information which is determined to be below the threshold value and the infrastructure 5 provided with the wireless tag 2 on the display 44 (ACT 5).

The sequence of the processing carried out in the embodiment may be different from that exemplarily described herein.

While certain embodiments have been described, these embodiments have been presented by way of example only, and are not intended to limit the scope of the invention. Indeed, the novel embodiments described herein may be embodied in a variety of other forms; furthermore, various omissions, substitutions and changes in the form of the embodiments described herein may be made without departing from the spirit of the invention. The accompanying claims and their equivalents are intended to cover such forms or modifications as would fall within the scope and spirit of the invention.

What is claimed is:

1. A monitoring system of a social infrastructure, comprising:
    a sensor configured to be arranged in the social infrastructure and detect one of a strain of the social infrastructure and a stress generated to the social infrastructure;
    a passive wireless tag configured to be arranged in the social infrastructure to send identification information and measurement information of the sensor by using received electromagnetic waves as a drive source;
    a reader which is installed in a vehicle and is configured to communicate with the wireless tag to acquire the identification information and the measurement information while the vehicle is operated;
    wherein the sensor is configured to detect at least the stress generated to the social infrastructure and the social infrastructure comprises a tunnel, and wherein the stress sensor detects stress applied to an internal wall of the tunnel; and
    a notification apparatus configured to acquire the identification information and the measurement information from the reader, detect the wireless tag or the social infrastructure serving as a notification target based on the identification information and the measurement information, and notify the notification target.

2. The monitoring system according to claim 1, wherein the sensor is enabled to operate by the power generated by the wireless tag.

3. A monitoring method, including:
    acquiring, using a reader which is installed in a vehicle, while the vehicle is operation, the identification information and the measurement information of a sensor from the a passive wireless tag which is arranged in a social infrastructure and is capable of communicating with the sensor arranged in the social infrastructure, wherein the sensor detects one of a strain of the social infrastructure and a stress generated to the social infrastructure;
    detecting at least the stress generated to the social infrastructure and the social infrastructure comprises a tunnel, and wherein the stress sensor detects stress applied to an internal wall of the tunnel;
    detecting the wireless tag or the social infrastructure serving as a notification target based on the identification information and the measurement information; and
    notifying the notification target.

* * * * *